US007622470B2

(12) United States Patent
O'Connor et al.

(10) Patent No.: US 7,622,470 B2
(45) Date of Patent: Nov. 24, 2009

(54) TREATMENT OF T-CELL LYMPHOMA USING 10-PROPARGYL-10-DEAZAAMINOPTERIN

(75) Inventors: Owen A. O'Connor, Scarsdale, NY (US); Francis M. Sirotnak, Hampton Bays, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 11/141,868

(22) Filed: May 31, 2005

(65) Prior Publication Data

US 2005/0267117 A1 Dec. 1, 2005

Related U.S. Application Data

(60) Provisional application No. 60/521,593, filed on May 30, 2004.

(51) Int. Cl.
*A61K 31/495* (2006.01)
(52) U.S. Cl. ..................... 514/249; 514/258
(58) Field of Classification Search .............. 514/249, 514/258
See application file for complete search history.

(56) References Cited

U.S. PATENT DOCUMENTS

| | | | |
|---|---|---|---|
| 4,393,064 A | 7/1983 | Degraw et al. | |
| 4,433,147 A | 2/1984 | Degraw et al. | |
| 4,652,533 A | 3/1987 | Jolley | |
| 4,843,155 A | 6/1989 | Chomczynski | |
| 5,354,751 A | 10/1994 | DeGraw et al. | |
| 5,981,592 A * | 11/1999 | Wechter et al. | 514/570 |
| 6,028,071 A * | 2/2000 | Sirotnak et al. | 514/249 |
| 6,323,205 B1 | 11/2001 | Sirotnak et al. | |
| 6,410,696 B1 | 6/2002 | Davalian et al. | |

FOREIGN PATENT DOCUMENTS

| WO | WO 98/02163 | * 1/1998 |
|---|---|---|
| WO | 2005/117891 A1 | 12/2005 |
| WO | 2005/117892 A1 | 12/2005 |

OTHER PUBLICATIONS

Matsuo et al., "Association between polymorphisms of folate- and methionine-metabolizing enzymes and susceptibility to malignant lymphoma", Blood, vol. 97, No. 10, pp. 3205-3209 (2001).*
Gerald D. Weinstein, "Diagnosis and Treatment: Drugs Five Years Later: Methotrexate", Annals of Internal Medicine, vol. 86, pp. 199-204 (1977).*
Grenzebach et al. Annals of Hematology, 2001, vol. 80, Suppl. 3, pp. B73-B76 (Abstract attached).*
Liang et al. Hematological Oncology, 1992, vol. 10, pp. 155-161 (Abstract attached).*
Fouchard et al: Leukemia, 1998, vol. 12, pp. 578-585 (Abstract attached).*
Au et al. British Journal of Dermatology, 2000, vol. 143, pp. 408-410.*
Starling et al, Drug trials in neuroblastoma: cyclophosphamide (NSC-26271) Alone; Vincristine (NSC-67574) plus cyclophosphamide; 6-mercaptopurine (NSC-755) plus 6-methylmercaptopurine riboside (NSC-40774); and cytosine arabinoside (NSC-63878) alone, Cancer Chemotherapy Reports, vol. 58, No. 5, p. 683-687, Sep./Oct. 1974.
DeGraw et al, Synthesis and antitumor activity of 10-propargyl-10-deazaaminopterin, Journal of Medicinal Chemistry, 1993.
Wang et al, Activity of a novel anti-folate (PDX, 10-propargyl 10-deazaaminopterin) against human lymphoma is superior to methotrexate and correlates with tumor rfc-1 gene expression, Leukemia & Lymphoma, vol. 44, p. 1027-1035, 2003.
Krug et al, 10-propargyl-10-deazaaminopterin: an antifolate with activity in patients with previously treated non-small cell lung cancer, Clinical Cancer Research, vol. 9, p. 2072-2078, Jun. 2003.
Awar, Omar et al. "Treatment of Transformed Mycosis Fungoides with Intermittent Low-Dose Gemcitabine." Oncology Sep. 23, 2007, pp. 103-135, vol. 73, Department of Internal Medicine.
Bekkenk, Marcel et al. "Peripheral T-Cell Lymphomas Unspecified Presenting in the Skin: Analysis of Prognostic Factors in a Group 82 Patients." Blood Sep. 13, 2003, pp. 2213-2219, vol. 102, No. 6, The American Society of Hematology.
Cheson, Bruce et al. "Report of an International Workshop to Standardize Response Criteria for Non-Hodgkin's Lymphoma's." 1999, pp. 1244-1253, vol. 117, No. 4, Journal of Clinical Oncology.
Howard, Michael et al. "Mycosis Fungoides: Classic Disease and Variant Presentations." 2000, pp. 91-99, vol. 19, No. 2, Departments of Pathology and Dermatology.
Mercadal, S. et al. "Intensive chemotherapy (high-dose CHOP/ESHAP regimen) followed by autologous stemOcell transplantation in previously untreated patients with peripheral T-cell lymphoma." Annals of Oncology 2008, pp. 958-963, vol. 19, Oxford University.
www.nccn.org "Non-Hodgkins's Lymphomas" V.3.2008, Apr. 10, 2008, National Comprehensive Cancer Network.
Olsen, Elise et al. "Revisions to the staging and classification of mycosis fungoides and Sezary syndrome: a proposal of the International Society for Cutaneous Lymphomas (ISCL) and the cutaneous lymphoma task force of the European Orginization of Research and Treatment of Cancer (EORTC)." Blood, Sep. 15, 2007, pp. 1713-1722, vol. 110, No. 6, The American Society if Hematology.
Prochazkova, Martina et al. "Large Cell Transformation of mycosis fungoides: tetraploidization within skin tumor large cells." Cancer Genetics and Cytogenetics 2005, pp. 1-6, vol. 163.

(Continued)

*Primary Examiner*—Ardin Marschel
*Assistant Examiner*—James D Anderson
(74) *Attorney, Agent, or Firm*—Larson & Anderson, LLC (57) ABSTRACT

T cell lymphoma is treated by administering to a patient suffering from T cell lymphoma a therapeutically effective amount of 10-propargyl-10-deazaaminopterin. Remission is observed in human patients, even with drug resistant T cell lymphoma at weekly dosages levels as low as 30 mg/m². In general, the 10-propargyl-10-deazaaminopterin is administered in an amount of from 30 to 275 mg/m² per dose.

161 Claims, 2 Drawing Sheets

OTHER PUBLICATIONS

Quereux, Gaelle et al. "Prospective Multicancer Study of Pegylated Liposomal Doxorubicin Treatment in Patients With Advanced or Refractory Mycosis Fungoides or Sezary Syndrome." Arch Dermatology 2008, pp. 727-733, vol. 144, No. 6.

Rodriguez-Abreu, Delvys et al. "Peripheral T-cell Lymphomas, unspecified (or not otherwise specified): a review." Hematol Oncol. 2008 pp. 8-20, vol. 26.

Rosen, Steven et al. "Primary Cutaneous T-Cell Lymphomas." 2006, pp. 323-330, American Society of Hematology.

Savage, K. et al. "Characterization of peropheral T-cell lymphomas in a single North American institution by the WHO classification." Annals of Oncology2004 pp. 1467-1475, vol. 15.

Vergier, Beatrice et al. "Transformation of mycosis fungoides: clinicopathological and prognostic features of 45 cases." Blood, Apr. 1, 2000, pp. 2212-2218, vol. 95, No. 6.

Vonderheid, Eric et al. "Treatment Planning in cutaneous T-Cell Lymphoma." Dermatologic Therapy 2003, pp. 276-282, vol. 16.

Wang, Eunice et al. "Activity of a Novel Anti-folate (PDX, 10-propargyl-10-deazaaminopterin) against Human Lymphoma is Superior to Methotrexate and Correlates with Tumor RFC-1 Gene Expression." Leukemia and Lymphoma 2003, pp. 1027-1035, vol. 44, No. 6.

Weidmann, E et al. "Diagnosis and actual therapy strategies in peripheral T-Cell lymphomas: summary of an international meeting." Annals of Oncology 2004, pp. 369-374, vol. 15.

Molina, Julian et al. "Pralatrexate, a dihydrofolate reductase inhibitor for the potential treatment of several malignancies." IDrugs, 2008, pp. 508-521, vol. 11, No. 7, Drug Profile.

"Methotrexate Injection, USP." Mayne, 2005, pp. 1-26.

Nair, M. et al. "Synthesis and Biological Evaluation of Poly-y-glutamyl Metabolites of 10-Deazaaminopterin and 10-Ethyl-10-deazaaminopterin." J. Med Chem. 1988, pp. 181-185, American Chemical Society.

O'Connor, Owen. "Developing new drugs for the Treatment of lymphoma." European Journal of Haematology, 2005, pp. 150-158, vol. 75 (Supp 66), Blackwell Munksgaard.

O'Connor, Owen et al. "A Phase '2-1-2' Study of Two Different Doses and Schedules of Pralatrexate, A High Affinity Substrate for the Reduced Folate Carrier (rfc-1), in Patients with Relapsed or Refactory Lymphoma Reveals Marked Activity in T-Cell Malignancies." AACR, 2007.

O'Connor, Owen et al. "Pralatrexate (PDX) Produces Durable Complete Remissions in Patients with Chemotherapy Resistant Precursor and Peripheral T-Cell Lymphomas: Results of the MSKCC Phase I/II Experience." Blood, 2006, pp. 1-2, vol. 108, American Society of Hematology, Abstract 400.

O'Connor, Owen et al. "Pralatrexate (10-propargyl-10-deazaaminopterin (PRX)), a Novel Antifolate, Effects Durable Complete Remissions (CR) in Patients with a Diversity of Drug Resistant T-Cell Lymphomas with Minimal Toxicity." Blood, 2005, pp. 1-2, vol. 106, American Society of Hematology, Abstract 2678.

O'Connor, Owen et al. "Pralatrexate, a novel class of antifol with high affinity for the reduced folate carrier type 1, produces marked complete and durable remissions in a diversity of chemotherapy refactory cases of T-cell lymphoma." Journal Compilation, 2007, pp. 425-428, vol. 139, Black well Publishing Ltd.

O'Connor, Owen. "Pralatrexate: an emerging new agent with activity in T-cell lymphomas." Current Opinion in Oncology, 2006, pp. 591-597, vol. 18, Lippincott Williams & Wilkins.

O'Connor, Owen et al. "Pralatrexate (PDX) Produces Durable Complete Remissions in Patients with Chemotherapy Resistant Precursor and Peripheral T-Cell Lymphomas: Results of the MSKCC Phase I/II Experience." Dec. 2006, Power Point Presentation, ASH.

Paulli, Marco et al. "Cutaneous T-cell Lymphoma (including rare subtypes). Current concepts. II." Haematologica, Nov. 2004, pp. 1372-1388, vol. 89, Malignant Lymphomas.

Rezania, Dorna et al. "The Diagnosis, Management, and Role of Hematopoietic Stem Cell Transplantation in Aggressive Peripheral T-Cell Neoplasms." Cancer Control, Apr. 2007, pp. 151-159, vol. 14, No. 2.

Rizvi, Mujahid et al. "T-cell non-hodgkin lymphoma." Blood, Feb. 15, 2006, pp. 1255-1264, vol. 107, No. 4, The American Society of Hematology.

Rots, Marianne et al. "Role of Folylpolyglutamate Synthetase and Folylpolyglutamate Hydrolase in Methotrexate Accumulation and Polyglutamylation in Childhood Leukemia." Blood, 1999, pp. 1677-1683, vol. 93, The American Society of Hematology.

Rots, M. et al. "mRna expression levels of methotrexate resistance-related proteins in childhood leukima as determined by a standardized competitive template-based RT-PCR method." Leukemia, 2000, pp. 2166-2175, vol. 14, Macmillan Publishers Ltd.

Rumberger, B et al. "Differing Specificities for 4-Aminofolate Analogues of Folylpolyglutamyl Synthetase from Tumors and Proliferative Intestinal Epithelium of the Mouse with Significance for Selective Antitumor Action." Cancer Research, Aug. 1, 1990, pp. 4639-4643, vol. 50.

Salhany, Kevin et al. "Transformation of Cutaneous T Cell Lymphoma to Large Cell Lymphoma." American Journal of Pathology, Aug. 2, 1988, pp. 265-277, vol. 132, No. 2, American Association of Pathologists.

Samuels, Lawrence et al. "Similar Differential for Total Polyglutamylation and Cytotoxicity among Various Folate Analogues in Human and Murine Tumor Cells in Vitro." Cancer Research, Apr. 1985, pp. 1488-1495, vol. 45, Presented in part at the 74th Annual Meeting of the American Association for Cancer Research.

Samuels, L et al. "Hydrolytic Cleavage of Methotrexate y-Polyglutamates by Folylpolyglutamyl Hydrolase Derived from Various Tumors and Normal Tissues of the Mouse." Cancer Research, May 1986, pp. 2230-2235, vol. 46.

Allos Therapeutics, Inc. "Allos Therapeutics Reports Interim Response and Safety Data from Pivotal Phase 2 Propel Trial." May 15, 2008 (Press Release).

Allos Therapeutics, Inc. "Results Reported at the American Society of Hematology Annual Meeting Affirm Impressive Activity of Allos Therapeutics' Novel Antifolate PDX in Patients with Peripheral T-Cell Lymphoma." Dec. 11, 2006 (Press Release).

Assaraf, Yehuda. "Molecular Basis of Anitfolate Resistance." Cancer Metastasis Rev., 2007. pp. 153-181, vol. 26, Springer.

Azzoli, Christopher et al. "A Phase 1 Study of Pralatrexate in Combination with Paclitaxel or Docetaxel in Patients with Advance Solid Tumors." Clin. Cancer Res. May 1, 2007, pp. 2692-2698, vol. 13, No. 9.

Barberio, E et al. "Transformed mycosis fungoides: clinicopathological features and outcome." British Journal of Dermatology, 2007, pp. 284-289, vol. 157, British Association of Dermatologists.

Barredo, Julio et al. "Differences in Constitutive and Post-Methotrexate Folylpolyglutamate Synthetase Activity in B-Lineage and T-Lineage Leukemia." Blood, Jul. 15, 1994, pp. 564-569, vol. 84, No. 2.

Burg, Gunter et al. "WHO/EORTC classification of cutaneous lymphomas 2005: histological and molecular aspects." Journal of Cutaneous Pathology, 2005, pp. 647-674, vol. 32, Blackwell Munksgaard.

Burg, Gunter et al. "Cutaneous Lymphomas Current and Future Concepts." J Egypt wom. Dermatol. Soc., 2007, pp. 1-23, vol. 4, No. 1.

Connors, Joseph et al. "Lymphoma of the Skin." Hematology, 2002, pp. 263-282, American Society of Hematology.

DeGraw, J. et al. "Synthesis and Antitumor Activity of 10-Alkyl-10-deazaaminopterins. A Convenient Synthesis of 10-Deazaaminopterin." J. Med. Chem. 1982, pp. 1227-1230,vol. 25, American Chemical Society.

DeGraw, Joseph et al. "New Analogs of Methotrexate in Cancer and Arthritis." Current Medicinal Chemistry, 1995, pp. 630-653, vol. 2, Bentham Science Publishers B.V.

Diamandidou, Eleni et al. "Transformation of Mycosis Fungoides/Sezary Syndrome: Clinical Characteristics and Prognosis." Blood, 1998, pp. 1150-1159, vol. 92, American Society of Hematology (From www.bloodjournal.org by on Jul. 21, 2008).

Diddens, Heyke et al. "Patterns of Cross-Resistance to the Antigolate Drugs Trimetrexate, Metoprine, Homofolate, and CB3717 in Human Lymphoma and Osteosarcoma Cells Resistant to Methotrexate." Cancer Research, Nov. 1983, pp. 5286-5292, vol. 43.

Dmitrovsky, Ethan et al. "Cytologic Transformation in Cutaneous T Cell Lymphoma: A Clinicopathologic Entity Associated With Poor Prognosis." Journal of Clinical Oncology, Feb. 1987, pp. 208-215, vol. 5, No. 2, The American Society of Clinical Oncology.

Fotoohi, Kambiz et al. "Disparate mechanisms of Antifolate resistance provoked by methotrexate and its ,metabolite 7-hydroxymethotrexate in leukemia cells: Implications for efficacy of methotrexate therapy." Blood, Aug. 12, 2004, pp. 1-32, American Society of Hematology.

Fry, David et al. "Biological and biochemical properties of new anticancer folate antagonists." Cancer and Metastasis Reviews, 1987, pp. 251-270, vol. 5, Martinus Nijoff Publishers, Boston.

Fury, Matthew et al. "A phase I clinical pharmacologic study of pralatrexate in combination with probenecid in adults with advanced solid tumors." Cancer Chemother Pharmacol. 2006, pp. 671-677, vol. 57, Springer-Verlag.

Galpin, Amy et al. "Differences in Folylpolyglutamate Synthetase and Dihydrofolate Reductase Expression in Human B-Lineage versus T-Lineage Leukemic Lymphoblasts: Mechanisms for Lineage Differences in Methotrexate Polyglutamylation and Cytotoxicity." Molecular Pharmacology, 1997, pp. 155-163, vol. 52, The American Society for Pharmacology and Experimental Therapuetics.

Gangjee, Aleem et al. "Effect of Bridge Region Variation on Antifolate and Antitumor Activity of Classical 5-Substituted 2,4-Diaminofuro [2,3-d] pyrimidines." J. Med. Chem. 1995, pp. 3798-3805, vol. 38, American Chemical Society.

Girardi, Michael et al. "The Pathogenesis of Mycosis Fungoides." The New England Journal of Medicine, May 6, 2004, pp. 1978-1988, vol. 350, No. 19, Massachusetts Medical Society.

Gisselbrecht, Christian et al. "Prognostic Significance of T-Cell Phenotype in Aggressive Non-Hodgkin's Lymphomas." Blood, Jul. 1, 1998, pp. 76-82, vol. 92, No. 1, The American Society of Hematology.

Grenzebach, J et al. "Favorable outcome for children and adolescents with T-cell lymphoblastic lymphoma with an intensive All-type therapy without local radiotherapy." Ann Hematol., 2001, pp. B73-B76, vol. 80, Springer-Verlag.

Hallermann, Christian et al. "Regulatory T-Cell phenotype in association with large cell transformation of mycosis fungoides." European Journal of Haematology, 2007, pp. 260-263, vol. 78, Blackwell Munksgaard.

Haynes, Harley et al. "Therapy of Mycosis Fungoides." Progress in Germatology, Mar. 1968, pp. 1-5, vol. 3, Dermatology Foundation.

Holm, Jan et al. "High and Low Affinity Binding of Folate to Proteins in Serum of Pregnant Women." Biochimica et Biophysica Acta, 1980, pp. 539-545, vol. 629, Elsevier/ North-Holland Biomedical Press.

Huennekens, F et al. "The Methotrexate Story: A Paradigm for Development of Cancer Chemotherapeutic Agents." Advan. Enzyme Regul. 1994, pp. 397-419, vol. 34, Elsevier Science Ltd.

Kamarashev, Jivko et al. "Mycosis fungoides—analysis of the duration of disease stages in patients who progress and the time point of high-grade transformation." International Journal of Dermatology, 2007, pp. 930-935, vol. 46, The International Society of Dermatology.

Khokhar, Nushmia et al. "Experimental Therapeutics with a New 10-Deazaaminopterin in Human Mesothelioma: Further Improving Efficacy through Structural Design, Pharmacologic Modulation at the Level of MRP ATPases and Combined Therapy with Platinums." Clinical Cancer Research. Oct. 2001, pp. 3199-3205, vol. 7.

Krug, Lee et al. "Phase II Trial of Pralatrexate (10-Propargyl-10-deazaaminopterin, PDX) in Patients with Unresectable Malignant Pleural Mesothelioma." Journal of Thoracic Oncology, Apr. 2007, pp. 317-320, vol. 2, No. 4.

Krug, Lee et al. "Phase I and Pharmacokinetic Study of 10-Propargyl-10-deazaaminopterin, a New Antifolate." Clinical Cancer Research, Sep. 2000, pp. 3493-3498, vol. 6.

Leclerc, Guy et al. "Analysis of folylpoly-y-glutamate synthetase gene expression in human B-precursor ALL and T-lineage ALL cells." BMC Cancer, May 2006, pp. 1-12, vol. 6, No. 132, BioMed Central.

Longo-Sorbello, Giuseppe et al. "Current understanding of methotrexate pharmacology and efficacy in acute leukemias. Use of newer antifolate in clinical trials." Hematologica, 2001, pp. 121-127, vol. 86, Trends in Hematology.

Lundin, Jeanette et al. "Therapy for Mycosis Fungoides." Current Treatment Option in Oncology, 2004, pp. 203-214, vol. 5, Current Science Inc.

McDonald, Charles et al. "Cutaneous uses of the antiproliferative drugs." American Society for Clinical Pharmacology and Therapeutics, American Society for Pharmacology and Experimental Therapeutics, Nov. 1974, pp. 1-8, vol. 16, No. 5, The C.V. Mosby Company.

Moccio, D.M et al. "Similar Specificity of Membrane Transport for Folate Analogues and Their Metabolites by Murine and Human Tumor Cells: A Clinically Directed Laboratory Study." Cancer Research, Jan. 1984, pp. 352-357, vol. 44.

Sarris, A et al. "Trimetrexate in Relapsed T-Cell Lymphoma With Skin Involvement." Journal of Clinical Oncology, Jun. 15, 2002, pp. 2876-2880, vol. 20, No. 12, The American Society of Clinical Oncology.

Savage, Kerry "Aggressive Peripheral T-Cell Lymphomas (Specified and Unspecified Types)". Hematology, 2005, pp. 267-277, American Society of Hematology.

Scott, Eugene et al. "Therapy of Mycosis Fungoides Lymphoma." Skin Cancer Panel,1968, pp. 553-557, J.B. Lippincott Company.

Siegel, Richard et al., "Primary Cutaneous T-Cell Lymphoma: Review and Current Concepts", Journal of Clinical Oncology, Aug. 15, 2000, pp. 2908-2925, vol. 18, No. 15, American Society of Clinical Oncology.

Sirotnak, Francis et al. "Analogs of tetrahydrofolate directed at folate-dependent purine biosynthetic enzymes. Characteristics of mediated entry and transport-related resistance in L1210 cells for 5,10-dideazatetrahydrofolate and two 10-alkyl derivatives", Biochemical Pharmacology, 1988, pp. 4775-4777, vol. 37, No. 24, Pergamon Press plc., Great Britain.

Sirotnak, Francis et al., "Stereospecificity at Carbon 6 of Formyltetrahydrofolate as a Competitive Inhibitor of Transport and Cytotoxicity of Methotrexate in Vitro", Biochemical Pharmacology, 1979, pp. 2993-2997, vol. 28, Pergamon Press Ltd., Great Britain.

Sirotnak, F. et al., "New folate analogs of the 10-deaza-aminopterin series Basis for structural design and biochemical and pharmacologic properties", Cancer Chemotherapy Pharmacology, 1984, pp. 18-25, vol. 12, Springer-Verlag.

Sirotnak, F. et al., "Markedly Improved Efficacy of Edatrexate Compared to Methotrexate in a High-Dose Regimen with Leucovorin Rescue against Metastatic Murine Solid Tumors", Cancer Research, Feb. 1, 1993, pp. 587-591, vol. 53.

Sirotnak, F. et al., "Co-administration of Probenecid, an Inhibitor of a cMOAT/MRP-like Plasma Membrane ATPase, Greatly Enhanced the Efficacy of a New 10-Deazaaminopterin against Human Solid Tumors in Vivo", Clinical Cancer Research, Sep. 2000, pp. 3705-3712, vol. 6.

Sirotnak, F. et al., "A new analogue of 10-deazaaminopterin with markedly enhanced curative effects against human tumor xenografts in mice", Cancer Chemotherapy Pharmacology, 1998, pp. 313-318, vol. 42, Springer-Verlag.

Skibola, Christine et al., "Genetic susceptibility to lymphoma", Haematologica/The Hematology Journal, 2007, pp. 960-969, vol. 92, No. 7.

Skibola, Christine et al., "Polymorphisms and haplotypes in folate-metabolizing genes and risk of non-Hodgkin lymphoma", Blood, 2004, pp. 2155-2162, vol. 104, www.bloodjournal.org.

Slater, D.N., "The new World Health Organization-European Organization for Research and Treatment of Cancer classification for cutaneous lymphomas: a practical marriage of two giants", British Journal of Dermatology, 2005, pp. 874-880, vol. 153, British Association of Dermatologists.

Takimoto, Chris, "New Antifolates: Pharmacology and Clinical Applications", Oncologist, 1996, pp. 68-81, vol. 1, www.TheOncologist.com.

Toner, Lorraine et al., The Schedule-Dependent Effects of the Novel Antifolate Pralatrexate and Gemcitabine Are Superior to Methotrexate and Cytarabine in Models of Human Non-Hodgkin's Lymphoma, Clin Cancer Res, Feb. 1, 2006, pp. 924-932, vol. 12, No. 3, www.aacrjournals.org.

Ueda, Takanori et al. "Inhibitory Action of 10-Deazaaminopterins and Their Polyglutamates on Human Thy,idylate Synthase." Molecular Pharmacology, 1986, pp. 149-153, vol. 30, The American Society for Pharmacology and Experimental Therapeutics.

Willemze, Rein et al., "WHO-EORTC classification for cutaneous lymphomas", Blood (www.bloodjournal.org), May 15, 2005, pp. 3768-3785, vol. 105, No. 10, The American Society of Hematology.

Wright, Joel et al., "Further studies on the interaction of nonpolyglutamatable aminopterin analogs with dihydrofolate reductase and the reduced folate carrier as determinants of in vitro antitumor activity", Biochemical Pharmacology, 2003, pp. 1427-1433, vol. 65, Elsevier.

Janeway-Travers. "Immunobiology: the immune system in health and disease" 1996, 2nd edition, Garland Pub.

Akutsu, M et al. "Schedule-dependent synergism and antagonism between methotrexate and cytarabine against human leukima cell lines in vitro." Leukima. Mar. 12, 2002, pp. 1808-1817, vol. 16.

Ausubel, Frederick et al. "Current Protocols in Molecular Biology." Current Protocol, 1987, vol. 2.

Cadman Ed et al. "Mechanism of Synergistic Cell Killing when Methotrexate Preceded Cytosine Arabinoside." J. Clin. Invest. 1979, pp. 788-797, vol. 64.

Chau, I et al. "Gemcitibine and its combination in the treatment of malignant lymphoma." Clinical Lymphoma, 2002, pp. 97-104, vol. 3, No. 11.

Hoovis, ML et al. "Enhancement of the Antiproliferative Action of 1-β-D-Arabinofuranosylcytosine by Methotrexate in Murine Leukemic Cells (L5178Y)." Cancer Research, 1973, pp. 521-525, vol. 33.

Sambrook, Joesph et al. "Molecular Cloning." A Labratory Manual, 1989, Cold Spring Harbor, Second Edition.

Vrhovac, Radovan et al. "A novel antifolate 10-propargyl-10-deazaaminopterin (PDX) displays synergistic effects with gemcitabine in non-Hodgkins lymphoma models in vitro and in vivo." 45th Annual Meeting of the American Soceity of Hematology, Nov. 16, 2003, p. 288b, vol. 102, No. 11.

Wang et al. "PDX, a novel Antifolate with Potent in Vitro and in Vivo Activity in Non-Hodgkin's Lymphoma." Developmental Hematology and the Program for Molecular Pharmacology and Experimental Therapeutics, Abstract 2565, 2001, vol. 98.

* cited by examiner

TREATMENT OF T-CELL LYMPHOMA USING 10-PROPARGYL-10-DEAZAAMINOPTERIN

This application claims priority from U.S. Provisional Application No. 60/521,593, filed May 30, 2004, which application is incorporated herein by reference.

This invention described in this application was supported by NIH Grants CA092074 and CA 0172(00). The government of the United States has certain rights in the invention.

BACKGROUND OF THE INVENTION

This application relates to the use of a combination of 10-propargyl-10-deazaaminopterin and in the treatment of T-cell lymphoma.

Figure 1:
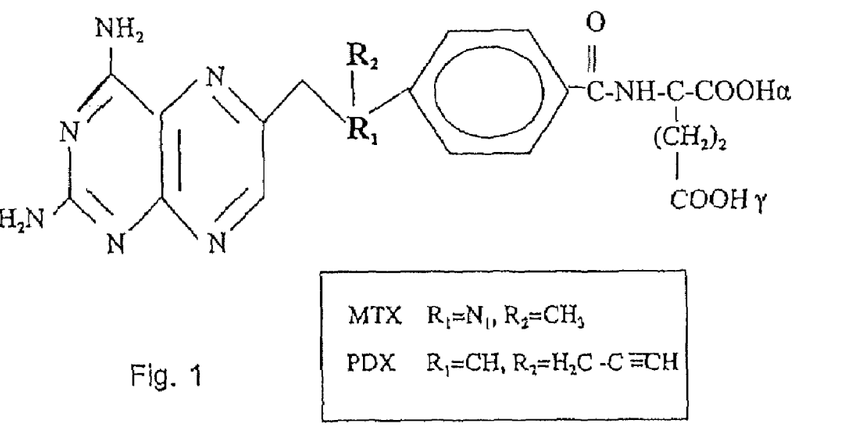
FIG. 1 shows the structure of PDX and methotrexate.

10-Propargyl-10-deazaaminopterin ("PDX" or "10-propargyl-10dAM") is a member of a large class of compounds which have been tested and in some cases found useful in the treatment of tumors. This compound, which has the structure shown in FIG. 1, was disclosed by DeGraw et al., "Synthesis and Antitumor Activity of 10-Propargyl-10-deazaaminopterin," *J. Medical Chem.* 36: 2228-2231 (1993) and shown to act as an inhibitor of growth in the murine L1210 cell line and to a lesser extent of the enzyme dihydrofolate reductase ("DHFR"). In addition, some results were presented for the antitumor properties of the compound using the E0771 murine mammary tumor model. This data was equivocal because of the small number of mice used in the test (3 per dosage), the absence of any standard deviation information which would quantify the reliability of the data, and the fact that the highest dose used was in fact toxic to the mice. Nevertheless, assuming this data has some predictive value for the efficacy of a drug in treating human tumors, it would at best predict a drug which, at equivalent levels of tolerance, had properties comparable to or perhaps slightly better than methotrexate.

PCT Publication No. WO98/02163, discloses the surprising observation that more highly purified PDX compositions when tested in a xenograft model for their efficacy against human tumors have now been shown to be far superior to methotrexate ("MTX") and are even superior to edatrexate ("ETX"), a more recent clinical candidate. Moreover, 10-propargyl-10dAM showed a surprising ability to cure tumors such that there was no evidence of tumor growth several weeks after the cessation of therapy. Thus, highly purified composition containing 10-propargyl-10dAM. can be used in accordance with the invention to treat tumors, including both solid tumors and leukemias. The composition is illustrated for use in treatment of human mammary tumors and human lung cancer.

Subsequent studies on PDX have shown that it is useful on its own and in combinations with other therapeutic agents. For example, Sirotnak et al., Clinical Cancer Research Vol. 6, 3705-3712 (2000) reports that co-administration of PDX and probenecid, an inhibitor of a cMOAT/MRP-like plasma membrane ATPase greatly enhances the efficacy of PDX against human solid tumors in vivo. PDX and combinations of PDX with platinum based chemotherapeutic agents have been shown to be effective against mesothelioma. (Khokar, et al., Clin. Cancer Res. 7: 3199-3205 (2001).

The term "lymphomas" refers to a variety of disease states, including Non-Hodgkins Lymphoma (NHL); diffuse large B-cell lymphoma (DLBCL); follicular lymphoma (FL); Hodgkin's Disease; Burkitt's Lymphoma; cutaneous T cell lymphoma; primary central nervous system lymphoma, and lymphomatous metastases. In most cases, lymphoma is characterized by the presence of cancerous B cells. However, in T cell lymphomas, the disease state is characterized by cancerous T lymphocytes.

SUMMARY OF THE INVENTION

In accordance with the present invention, T cell non-Hodgkin's lymphoma is treated using PDX. Thus, in accordance with one aspect of the invention, a method is provided for the treatment of T cell non-Hodgkin's lymphoma comprising administering to a patient suffering from lymphoma a therapeutically effective amount of PDX. Preliminary clinical results in humans have shown this treatment to be particularly effective, even with respect to the lymphomas that were refractory to other therapeutic modalities.

DETAILED DESCRIPTION OF THE INVENTION

This application relates to the use of 10-propargyl-10-deazaaminopterin in the treatment of T-cell lymphoma.

T-cell lymphomas are lymphomas in which the T cells of the patient are determined to be cancerous. T cell lymphomas encompass a variety of conditions including without limitation:

(a) lymphoblastic lymphomas in which the malignancy occurs in primitive lymphoid progenitors from the thymus;

(b) mature or peripheral T cell neoplasms, including T cell prolymphocytic leukemia, T-cell granular lymphocytic leukemia, aggressive NK-cell leukemia, cutaneous T cell lymphoma (Mycosis fungoides/Sezary syndrome), anaplastic large cell lymphoma, T cell type, enteropathy-type T cell lymphoma, Adult T-cell leukemia/lymphoma including those associated with HTLV-1, and angioimmunoblastic T cell lymphoma, and subcutaneous panniculitic T cell lymphoma; and (c) peripheral T cell lymphomas that initially involve a lymph node paracortex and never grow into a true follicular pattern.

In one embodiment of the invention, the composition comprises "highly purified" PDX. As used in the specification and claims hereof, compositions which are "highly purified" contain PDX substantially free of other folic acid derivatives, particularly 10-deazaaminopterin, which can interfere with the antitumor activity of the PDX. A composition within the scope of the invention may include carriers or excipients for formulating the PDX into a suitable dosage unit form for therapeutic use, as well as additional, non-folate therapeutic agents.

Figure 2:
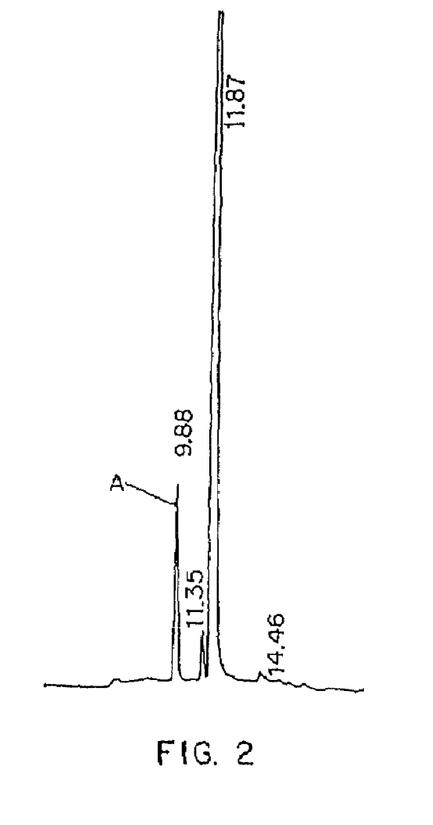
FIG. 2 shows an HPLC of an impure 10-propargyl-10-dAM preparation prepared in accordance with the prior art.

PDX can be synthesized using the method disclosed in the DeGraw paper, supra or in Example 7 of U.S. Pat. No. 5,354,751, which is incorporated herein by reference. HPLC evaluation of the product prepared by this method shows the presence of a substantial amount (~4.6%) of an impurity A (FIG. 2) which has a retention time consistent with 10-deazaaminopterin. Thus, if this synthetic approach is employed further purification is necessary beyond that disclosed in the DeGraw et al. paper. Such purification can be carried out by additional HPLC or crystallization to remove the 10-deazaaminopterin and other folic acid derivatives which may be present.

As reflected in U.S. Pat. No. 5,354,791 cited above, the 10-deazaaminopterin compound of the current invention (e.g., 10-propargyl-10-deazaaminopterin) can be formulated in the form of an acid addition salt. These salts are formed with one or more free NH2 groups of the heteroaroyl-10-deazaaminopterin molecule. Typically, the compounds are injected in the form of their sodium salts in aqueous solution. Other salts, such as K, Ca, $NH_4$, and the like, could be used as prepared from the appropriate hydroxide or carbonates.

The acid addition salts are the pharmaceutically acceptable, nontoxic addition salts with suitable acids, such as those with inorganic acids, for example, hydrochloric, hydrobromic, nitric, sulphuric, and phosphoric acids, and with organic acids, such as organic carboxylic acids, for example, glycolic, maleic, hydroxymaleic, malic, tartaric, citric, salicylic, acetyloxybenzoic, nicotinic, and isonicotinic acid, and organic sulphonic acids, for example, methanesulphonic, ethanesulphonic, 2-hydroxyethanesulphonic, toluene-p-sulphonic, and naphthalene-2-sulphonic acid.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate, with ammonia; or with a hydroxyl ion exchange resin, or with any other suitable reagent. An acid addition salt may also be converted into another acid addition salt according to known methods, for example, a salt with an inorganic acid may be treated with a metal salt, for example a sodium, barium or silver salt, of an acid in a suitable diluent, in which a resulting inorganic salt is insoluble and is thus removed from the reaction medium. An acid-addition salt may also be converted into another acid addition salt by treatment with an anion exchange preparation.

The glutamic acid COOH groups can also be in salt form, as the ammonium $NH_4$, alkali metal salts ($Na^+$, $K^+$), or the nontoxic alkaline earth metal salts ($Ca^{++}$) of the glutamate COOH groups. The 10-deazaaminopterin compound (e.g., 10-propargyl-10-deazaaminopterin) or salt thereof can be administered to the mammal, including human, by any available route, including oral and parenteral (intravenous, intraperitoneal, subcutaneous, and intramuscular) administration.

Figure 3:
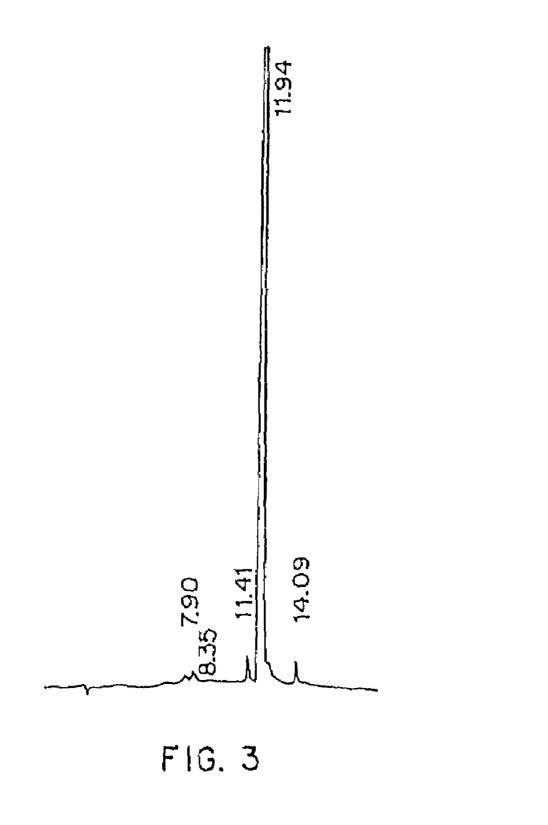
FIG. 3 shows an HPLC of a highly purified PDX preparation in accordance with the invention.

FIG. 3 shows an HPLC of a highly purified preparation consisting essentially of 10-propargyl-10-dAM in accordance with the invention prepared using the method described in Example 1. In this case, the amount of PDX (as determined by HPLC peak area) approaches 98%, and the peak corresponding to 10-deazaaminopterin is not detected by the processing software although there is a minor baseline ripple in this area.

PDX has been used in a Phase I/II study in which patients with aggressive lymphoma were enrolled, including three patients with drug-resistant T cell lymphoma. The following case summaries have been obtained. Each of these patients was also treated with folic acid (1 mg/m² daily starting 1 week prior to treatment with PDX) and B12 (1 mg/m² monthly) supplementation.

Patient 1
Diagnosis: Peripheral T-cell Lymphoma, Stage IV
Demographics: 48 Year old male
Prior Treatment: CHOP×4 cycles (July 2002-November 2002)—refractory ICE×2 cycles (December 2002)—refractory Campath (March 2003-June 2003)—mixed response
Pre-Treatment Staging: Extensive disease cutaneous disease
Treatment on Study: PDX 135 mg/m²×1 dose
Toxicities: Grade 3 stomatitis; neutropenia grade 3; sepsis
Response: Essentially complete remission by PET scan
Comment: This patient ultimately died after developing a bacteremia and sepsis from open skin lesions with Gram positive bacteria.

Patient 2
Diagnosis: Lymphoblastic Lymphoma, Precursor T-cell, Stage IV
Demographics: 65 year old female
Prior Treatment: L20—Complex combination chemotherapy since May 2002, administered over two years. Has received MTX from May 2002 through February 2004. Relapsed December 2004.
Pre-Treatment Staging: Extensive widespread relapse
Treatment on Study: PDX 30 mg/m²×3 weeks every 4 weeks. Completed 3 cycles to date
Toxicities: None
Response: Complete remission by PET and CT scans
Comment: Patient with essentially methotrexate resistant disease with extensive sinus based disease which began resolving after one dose of PDX.

Patient 3
Diagnosis: HTLV Associated T-cell Lymphoma
Demographics: 38 Year old male
Prior Treatment: EPOCH—infusional combination chemotherapy October 2003 to February 2004
Pre-Treatment Staging: Left axillary disease
Treatment on Study: PDX 30 mg/m² weekly×3 every 4 weeks×2 cycles
Toxicities: None
Response: Complete remission
Comment: Complete disappearance of clinically evident disease by the end of the first cycle, very well tolerated, no toxicity.

Patient 4
Diagnosis: Panniculitic T-cell Lymphoma
Demographics: 25 Year old male
Prior Treatment: Ontak (refractory), September 2002-November 2002; Targretin and IFN α January 2003-October 2003 (durable partial remission); CHOP April 2004-June 2004; ICE June 2004, CyPen July 2004-August 2004, Targretin/MTX September 2004 to February 2005
Treatment on Study: PDX 30 mg/m² weekly×4
Response: Clinical complete remission by PET
Toxicities: None
Comment: healing subcutaneous lesions, too numerous to count, large ulcerative granulating lesion To date, only 4 patients with T-cell lymphoma have ever been treated with PDX, and all four have met criteria for complete remission, even based on the sensitive PET imaging techniques. Interestingly, the patient treated at 135 mg/m² received only a single dose of drug with a dramatic response to therapy, while the others had received only small modest doses on a weekly schedule.

For use in the present invention, PDX is advantageously formulated as part of a pharmaceutical preparation. The specific dosage form will depend on the method of administration, but may include tablets, capsules, oral liquids, and injectable solutions for intravenous, intramuscular or intraperitoneal administration. One suitable dosing schedule involves the administration of 150 mg/m$^2$ every two weeks. Lower levels may of course be indicated depending on the tolerance of an individual patient, or if more frequent administration were adopted. For example, levels on the order of 40 to 120 mg/m$^2$ of body surface area/day are appropriate. Dosages of 30 mg/m$^2$ weekly for 3 weeks followed by a one week rest, 30 mg/m$^2$ weekly×6 weeks followed by a one week rest, or gradually increasing doses of PDX on the weekly×6 week schedule are also suitable. Higher levels could be utilized if less frequent administration were used. Thus, in a general sense, dosages of 30 to 275 mg/m$^2$ are suitably used with various dosing schedules, for example 135 to 275 mg/m$^2$ for biweekly dosages, and 30 to 150 mg/m$^2$ for weekly dosages. The determination of suitable dosages using protocols similar to those described in U.S. Pat. No. 6,323,205, which is incorporated herein by reference, is within the skill in the art.

PDX may be used in combinations with other cytotoxic and antitumor compounds, including vinca alkaloids such as vinblastine, navelbine and vindesine; probenicid, nucleotide analogs such as gemcitabine, 5-fluorouracil, and cytarabine; alkylating agents such as cyclophosphamide or ifosfamide; cisplatin or carboplatin; leucovorin; taxanes such a paclitaxel or docetaxel; anti-CD20 monoclonal antibodies, with or without radioisotopes, and antibiotics such as doxorubicin and mitomycin. Combinations of PDX with several of these other antitumor agents or with growth factor inhibitors and anti-angiogenic agents may also be used.

PDX and other agents may be concurrently administered or utilized in combination as part of a common treatment regimen, in which the PDX and the other agent(s) are administered at different times. For example, the other agent may be administered before, immediately afterward or after a period of time (for example 24 hours) relative to the PDX administration. Thus, for purposes of this application, the term administering refers generally to concurrent administration or to sequential administration of the drugs and in either order in a parallel treatment regimen with or without a separation in time between the drugs unless otherwise specified.

PDX is suitably used in combination with folic acid and vitamin B12 supplementation to reduce the side effects of the treatment. For example, patients may be treated with folic acid (1 mg/m$^2$ daily starting 1 week prior to treatment with PDX) and B12 (1 mg/m$^2$ monthly).

EXAMPLE 1

Figure 4:
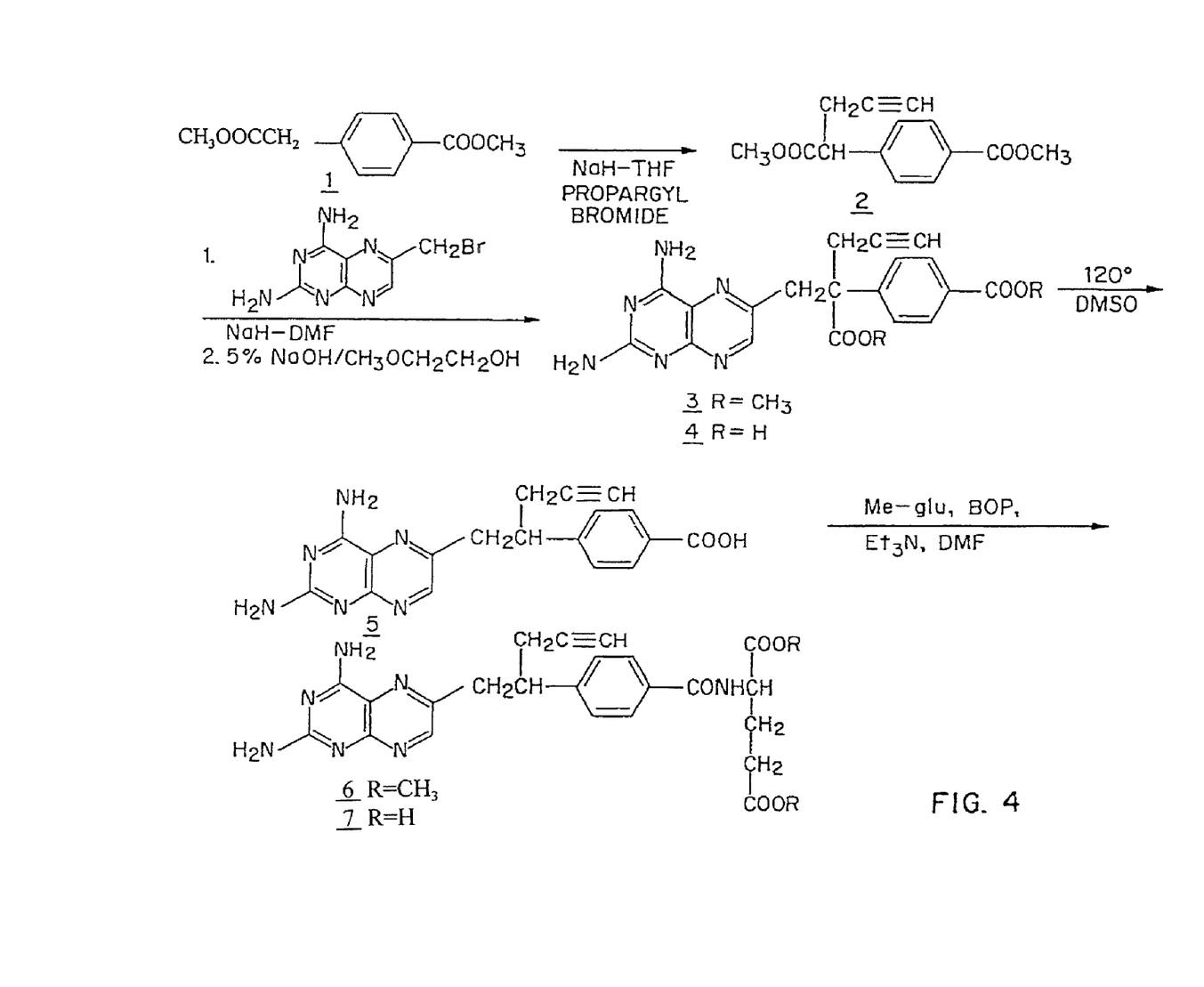
FIG. 4 shows a synthetic scheme useful in preparing the compound in accordance with the invention.

FIG. 4 shows a synthetic scheme useful in preparing 10-propargyl-10-dAM in accordance with the invention. A mixture of 60% NaH in oil dispersion (1.06 g, 26.5 mmol) in 18 mL of sieve-dried THF was cooled to 0° C. The cold mixture was treated with a solution of homoterephthalic acid dimethyl ester (5.0 g, 24 mmol. compound 1 in FIG. 4) in dry THF (7 mL), and the mixture was stirred for 1 hour at 0° C. Propargyl bromide (26.4 mmol) was added, and the mixture was stirred at 0° C. for an additional 1 hour, and then at room temperature for 16 hours. The resulting mixture was treated with 2.4 mL of 50% acetic acid and then poured into 240 mL of water. The mixture was extracted with ether (2×150 mL). The ether extracts were combined, dried over Na$_2$SO$_4$, and concentrated to an orange-yellow oil. Chromatography on silica gel (600 mL of 230-400 mesh) with elution by cyclohexane-EtOAc (8:1) gave the product α-propargylhomoterephthalic acid dimethyl ester (compound 2) as a white solid (4.66) which appeared by TLC (cyclohexane-EtOAc, 3:1) to be homogeneous. Mass spectral data on this product, however, showed it to be a mixture of the desired product 2, and the dipropargylated compound. No starting material 1 was detected. HPLC shows the ratio of mono- to di-propargylated products to be about 3:1. Since the dipropargylated product, unlike compound 1, cannot produce an unwanted coproduct in the next step of the reaction, this material was suitable for conversion to compound 3. Absence of starting compound 1 in the product used to proceed in the synthesis is very important in order to avoid the sequential formation of 10-dAM during the transformations lading to the final product, because complete removal from 10-dAM from 10-propargyl-1-dAM is very difficult.

A mixture was formed by combining 0.36 g of a 60% NaH (9 mmol) in oil dispersion with 10 mL of dry DMF and cooled to 0-5° C. The cold mixture was treated drop-wise with a solution of the product of the first reaction (compound 2) (2.94 g, 12 mmol) in 10 mL dry DMF and then stirred at 0° C. for 30 minutes. After cooling to −25° C., a solution of 2,4, diamino-6-(bromomethyl)-pteridine hydrobromide-0.2 2-propanol (1.00 g, 2.9 mmol) in 10 mL dry DMF was added drop-wise while the temperature was maintained near −25° C. The temperature of the stirred mixture was allowed to rise to −10° C. over a period of 2 hours. After an additional 2 hours at −10° C., the temperature was allowed to rise to 20° C.; stirring at room temperature was continued for 2 hours longer. The reaction was then adjusted to pH 7 by addition of solid CO$_2$, After concentration in vacuo to remove solvent, the residue was stirred with diethyl ether and the ether insoluble material was collected, washed with water, and dried in vacuo to give 1.49 g of a crude product. This crude product was dissolved in CHCl$_3$-MeOH (10:1) for application to a silica gel column. Elution by the same solvent system afforded 10-propargyl-10-carbomethoxy-4-deoxy-4-amino-10-deazapteroic acid methyl ester (compound 3) which was homogenous to TLC in 40% yield (485 mg).

A stirred suspension of compound 3 (400 mg, 0.95 mmol) in 2-methoxyethanol (5 mL) was treated with water (5 mL) and then 10% sodium hydroxide solution (3.9 mL). The mixture was stirred as room temperature for 4 hours, during which time solution occurred. The solution was adjusted to pH 8 with acetic acid and concentrated under high vacuum. The resulting residue was dissolved in 15 mL of water and acidified to pH 5.5-5.8 resulting in formation of a precipitate. The precipitate was collected, washed with water and dried in vacuo to recover 340 mg of compound 4 (91% yield). HPLC analysis indicated a product purity of 90%.

Compound 4 (330 mg) was decarboxylated by heating in 15 mL DMSO at 115-120° C. for 10 minutes. A test by HPLC after 10 minutes confirmed that the conversion was essentially complete. DMSO was removed by distillation in vacuo (bath at 40° C.). The residue was stirred with 0.5 N NaOH to give a clear solution, Acidification to pH 5.0 with 1N HCl gave 10-propargyl-4-deoxy-4-amino-10-deazapteroic acid (compound 5) as a yellow solid in 70% yield. HPLC indicated product purity at this stage as 90%.

Compound 5 (225 mg, 0.65 mmol) was coupled with dimethyl L-glutamate hydrochloride (137 mg, 0.65 mmol) using BOP reagent (benzotriazole-1-yloxytris(dimethylamino) phosphonium hexafluorophosphate (287 mg, 0.65 mmol, Aldrich Chemical Co.) in DMF (10 mL) containing triethylamine (148 mg, 1.46 mmol). The mixture was stirred for 3 hours at 20-25° C. and then evaporated to dryness. The residue was stirred with water, and the water-insoluble crude product was collected and dried in vacuo. The crude product (350 mg) was purified by silica gel chromatography with elution by CHCl$_3$-MeOH (10:1) containing triethylamine (0.25% by volume) to recover 165 mg of 10-propargyl-10-deazaaminopterin dimethyl ester (compound 6, 50% yield) which was homogeneous to TLC (CHCl$_3$-MeOH 5:1).

Compound 6 (165 mg, 0.326 mmol) was suspended in 10 mL stirred MeOH to which 0.72 mL (0.72 meq) 1N NaOH was added. Stirring at room temperature was continued until solution occurred after a few hours. The solution was kept at 20-25° C. for 8 hours, then diluted with 10 mL water. Evaporation under reduced pressure removed the methanol, and the concentrated aqueous solution was left at 20-25° C. for another 24 hours. HPLC then showed the ester hydrolysis to be complete. The clear aqueous solution was acidified with acetic acid to pH 4.0 to precipitate 10-propargyl-10-deazaaminopterin as a pale yellow solid, The collected, water washed and dried in vacuo product weighed 122 mg (79% yield). Assay by elemental analysis, proton NMR and mass spectroscopy were entirely consistent with the assigned structure. HPLC analysis indicated purity of 98% and established the product to be free of 10-deazaaminopterin.

What is claimed is:

1. A method for treatment of peripheral T cell lymphoma excluding mycosis fungoides comprising administering to a human having a peripheral T cell lymphoma other than mycosis fungoides a composition comprising a therapeutically effective amount of 10-propargyl-10-deazaaminopterin.

2. A method for treatment of peripheral T cell lymphoma excluding mycosis fungoides comprising administering to a human having a peripheral T cell lymphoma other than mycosis fungoides a composition comprising a therapeutically effective amount of 10-propargyl-10-deazaaminopterin, wherein the composition is formulated with 10-propargyl-10-deazaaminopterin substantially free of 10-deazaaminopterin.

3. The method of claim 1, wherein the 10-propargyl-10-deazaaminopterin is administered in an amount of from 30 to 275 mg/m$^2$ per dose.

4. The method of claim 3, wherein the 10-propargyl-10-deazaaminopterin is administered weekly.

5. The method of claim 4, wherein the 10-propargyl-10-deazaaminopterin is administered in an amount of 30 mg/m$^2$ per dose.

6. The method of claim 4, wherein the 10-propargyl-10-deazaaminopterin is administered in an amount of from 30 to 150 mg/m$^2$ per dose.

7. The method of claim 1, wherein the 10-propargyl-10-deazaaminopterin is administered biweekly.

8. The method of claim 7, wherein the 10-propargyl-10-deazaaminopterin is administered in an amount of from 135 to 275 mg/m$^2$ per dose.

9. The method of claim 2, wherein the 10-propargyl-10-deazaaminopterin is administered in an amount of from 30 to 275 mg/m$^2$ per dose.

10. The method of claim 2, wherein the 10-propargyl-10-deazaaminopterin is administered weekly.

11. The method of claim 10, wherein the 10-propargyl-10-deazaaminopterin is administered in an amount of 30 mg/m$^2$ per dose.

12. The method of claim 10, wherein the 10-propargyl-10-deazaaminopterin is administered in an amount of from 30 to 150 mg/m$^2$ per dose.

13. The method of claim 2, wherein the 10-propargyl-10-deazaaminopterin is administered biweekly.

14. The method of claim 13, wherein the 10-propargyl-10-deazaaminopterin is administered in an amount of from 135 to 275 mg/m$^2$ per dose.

15. The method of claim 1, wherein the peripheral T cell lymphoma is an a Human T-lymphotropic virus (HTLV) Associated T-cell Lymphoma/leukemia.

16. The method of claim 15, wherein the composition is formulated with 10-propargyl-10-deazaaminopterin substantially free of 10-deazaaminopterin.

17. The method of claim 16, wherein the 10-propargyl-10-deazaaminopterin is administered in an amount of from 30 to 275 mg/m$^2$ per dose.

18. The method of claim 16, wherein the 10-propargyl-10-deazaaminopterin is administered weekly.

19. The method of claim 18, wherein the 10-propargyl-10-deazaaminopterin is administered in an amount of 30 mg/m$^2$ per dose.

20. The method of claim 18, wherein the 10-propargyl-10-deazaaminopterin is administered in an amount of from 30 to 150 mg/m$^2$ per dose.

21. The method of claim 16, wherein the 10-propargyl-10-deazaaminopterin is administered biweekly.

22. The method of claim 21, wherein the 10-propargyl-10-deazaaminopterin is administered in an amount of from 135 to 275 mg/m$^2$ per dose.

23. The method of claim 1, wherein the peripheral T cell lymphoma is a subcutaneous Panniculitic T-cell Lymphoma.

24. The method of claim 23, wherein the composition is formulated with 10-propargyl-10-deazaaminopterin substantially free of 10-deazaaminopterin.

25. The method of claim 24, wherein the 10-propargyl-10-deazaaminopterin is administered in an amount of from 30 to 275 mg/m$^2$ per dose.

26. The method of claim 24, wherein the 10-propargyl-10-deazaaminopterin is administered weekly.

27. The method of claim 26, wherein the 10-propargyl-10-deazaaminopterin is administered in an amount of 30 mg/m$^2$ per dose.

28. The method of claim 26, wherein the 10-propargyl-10-deazaaminopterin is administered in an amount of from 30 to 150 mg/m$^2$ per dose.

29. The method of claim 24, wherein the 10-propargyl-10-deazaaminopterin is administered biweekly.

30. The method of claim 29, wherein the 10-propargyl-10-deazaaminopterin is administered in an amount from 135 to 275 mg/m$^2$ per dose.

31. The method of claim 1, wherein the peripheral T cell lymphoma is selected from: T cell prolymphocytic leukemia; T-cell granular lymphocytic leukemia; aggressive NK-cell leukemia; cutaneous T cell lymphoma excluding mycosis fungoides; anaplastic large cell lymphoma, T cell type; enteropathy-type T cell lymphoma; Adult T-cell leukemia/lymphoma; angioimmunoblastic T cell lymphoma; subcutaneous panniculitic T cell lymphoma; and peripheral T cell lymphomas that initially involve a lymph node paracortex and never grow into a true follicular pattern.

32. The method of claim 31, wherein the composition is formulated with 10-propargyl-10-deazaaminopterin substantially free of 10-deazaaminopterin.

33. The method of claim 32, wherein the 10-propargyl-10-deazaaminopterin is administered in an amount of from 30 to 275 mg/m$^2$ per dose.

34. The method of claim 32, wherein the 10-propargyl-10-deazaaminopterin is administered weekly.

35. The method of claim 34, wherein the 10-propargyl-10-deazaaminopterin is administered in an amount of 30 mg/m$^2$ per dose.

36. The method of claim 34, wherein the 10-propargyl-10-deazaaminopterin is administered in an amount of from 30 to 150 mg/m$^2$ per dose.

37. The method of claim 32, wherein the 10-propargyl-10-deazaaminopterin is administered biweekly.

38. The method of claim 37, wherein the 10-propargyl-10-deazaaminopterin is administered in an amount of from 135 to 275 mg/m$^2$ per dose.

39. The method of claim 1, wherein the human treated has relapsed or refractory peripheral T cell lymphoma.

40. The method of claim 39, wherein the 10-propargyl-10-deazaaminopterin is administered in an amount of from 30 to 275 mg/m$^2$ per dose.

41. The method of claim 39, wherein the 10-propargyl-10-deazaaminopterin is administered weekly.

42. The method of claim 41, wherein the 10-propargyl-10-deazaaminopterin is administered in an amount of 30 mg/m$^2$ per dose.

43. The method of claim 41, wherein the 10-propargyl-10-deazaaminopterin is administered in an amount of from 30 to 150 mg/m$^2$ per dose.

44. The method of claim 39, wherein the 10-propargyl-10-deazaaminopterin is administered biweekly.

45. The method of claim 44, wherein the 10-propargyl-10-deazaaminopterin is administered in an amount of from 135 to 275 mg/m$^2$ per dose.

46. The method of claim 39, wherein the 10-propargyl-10-deazaaminopterin is administered in one or more cycles, each cycle comprising administration once weekly for six weeks in an amount of from 30 to 150 mg/m$^2$ per dose followed by a one week rest.

47. The method of claim 46, wherein the 10-propargyl-10-deazaaminopterin is administered in an amount of 30 mg/m$^2$ per dose.

48. The method of claim 39, wherein the composition is formulated with 10-propargyl-10-deazaaminopterin substantially free of 10-deazaaminopterin.

49. The method of claim 48, wherein the 10-propargyl-10-deazaaminopterin is administered in an amount of from 30 to 275 mg/m$^2$ per dose.

50. The method of claim 48, wherein the 10-propargyl-10-deazaaminopterin is administered weekly.

51. The method of claim 50, wherein the 10-propargyl-10-deazaaminopterin is administered in an amount of 30 mg/m$^2$ per dose.

52. The method of claim 50, wherein the 10-propargyl-10-deazaaminopterin is administered in an amount of from 30 to 150 mg/m$^2$ per dose.

53. The method of claim 48, wherein the 10-propargyl-10-deazaaminopterin is administered biweekly.

54. The method of claim 53, wherein the 10-propargyl-10-deazaaminopterin is administered in an amount of from 135 to 275 mg/m$^2$ per dose.

55. The method of claim 2, wherein the 10-propargyl-10-deazaaminopterin is administered in one or more seven-week cycles, each cycle comprising administration once weekly for six weeks in an amount of from 30 to 150 mg/m$^2$ per dose followed by a one week rest.

56. The method of claim 55, wherein the 10-propargyl-10-deazaaminopterin is administered in an amount of 30 mg/m$^2$ per dose.

57. The method of claim 32, wherein the 10-propargyl-10-deazaaminopterin is administered in one or more seven-week cycles, each cycle comprising administration once weekly for six weeks in an amount of from 30 to 150 mg/m$^2$ per dose followed by a one week rest.

58. The method of claim 57, wherein the 10-propargyl-10-deazaaminopterin is administered in an amount of 30 mg/m$^2$ per dose.

59. The method of claim 48, wherein the 10-propargyl-10-deazaaminopterin is administered in one or more seven-week cycles, each cycle comprising administration once weekly for six weeks in an amount of from 30 to 150 mg/m$^2$ per dose followed by a one week rest.

60. The method of claim 59, wherein the 10-propargyl-10-deazaaminopterin is administered in an amount of 30 mg/m$^2$ per dose.

61. The method of claim 55, further comprising supplementation with folic acid and vitamin $B_{12}$.

62. The method of claim 57, further comprising supplementation with folic acid and vitamin $B_{12}$.

63. The method of claim 59, further comprising supplementation with folic acid and vitamin $B_{12}$.

64. The method of claim 31, wherein the peripheral T cell lymphoma is Sézary syndrome.

65. The method of claim 31, wherein the peripheral T cell lymphoma is Adult T cell leukemia/lymphoma associated with Human T-lymphotropic virus-1 (HTLV-1).

66. The method of claim 31, wherein the composition is administered as an oral liquid or as an injectable solution.

67. The method of claim 1, wherein the composition is administered as an oral liquid or as an injectable solution.

68. The method of claim 2, wherein the composition is administered as an oral liquid or as an injectable solution.

69. A method for treatment of peripheral T cell lymphoma excluding mycosis fungoides comprising administering to a human having a peripheral T cell lymphoma other than mycosis fungoides a composition comprising a therapeutically effective amount of a salt form of 10-propargyl- 10-deazaaminopterin.

70. The method of claim 69, wherein the 10-propargyl-10-deazaaminopterin is administered in an amount of from 30 to 275 mg/m$^2$ per dose.

71. The method of claim 69, wherein the 10-propargyl-10-deazaaminopterin is administered weekly.

72. The method of claim 71, wherein the 10-propargyl-10-deazaaminopterin is administered in an amount of 30 mg/m$^2$ per dose.

73. The method of claim 71, wherein the 10-propargyl-10-deazaaminopterin is administered in an amount of from 30 to 150 mg/m$^2$ per dose.

74. The method of claim 69, wherein the 10-propargyl-10-deazaaminopterin is administered biweekly.

75. The method of claim 74, wherein the 10-propargyl-10-deazaaminopterin is administered in an amount of from 135 to 275 mg/m$^2$ per dose.

76. The method of claim 69, wherein the peripheral T cell lymphoma is a Human T-lymphotropic virus (HTLV) Associated T-cell Lymphoma/leukemia.

77. The method of claim 76, wherein the composition is administered as an oral liquid or injectable solution.

78. The method of claim 76, wherein the 10-propargyl-10-deazaaminopterin is administered in an amount of from 30 to 275 mg/m$^2$ per dose.

79. The method of claim 76, wherein the 10-propargyl-10-deazaaminopterin is administered weekly.

80. The method of claim 79, wherein the 10-propargyl-10-deazaaminopterin is administered in an amount of 30 mg/m$^2$ per dose.

81. The method of claim 79, wherein the 10-propargyl-10-deazaaminopterin is administered in an amount of from 30 to 150 mg/m$^2$ per dose.

82. The method of claim 76, wherein the 10-propargyl-10-deazaaminopterin is administered biweekly.

83. The method of claim 82, wherein the 10-propargyl-10-deazaaminopterin is administered in an amount of from 135 to 275 mg/m² per dose.

84. The method of claim 69, wherein the peripheral T cell lymphoma is a subcutaneous Panniculitic T-cell Lymphoma.

85. The method of claim 84, wherein the composition is administered an oral liquid or as an injectable solution.

86. The method of claim 84, wherein the 10-propargyl-10-deazaaminopterin is administered in an amount of from 30 to 275 mg/m² per dose.

87. The method of claim 84, wherein the 10-propargyl-10-deazaaminopterin is administered weekly.

88. The method of claim 86, wherein the 10-propargyl-10-deazaaminopterin is administered in an amount of 30 mg/m² per dose.

89. The method of claim 86, wherein the 10-propargyl-10-deazaaminopterin is administered in an amount of from 30 to 150 mg/m² per dose.

90. The method of claim 84, wherein the 10-propargyl-10-deazaaminopterin is administered biweekly.

91. The method of claim 90, wherein the 10-propargyl-10-deazaaminopterin is administered in an amount from 135 to 275 mg/m² per dose.

92. The method of claim 69, wherein the peripheral T cell lymphoma is selected from: T cell prolymphocytic leukemia; T-cell granular lymphocytic leukemia; aggressive NK-cell leukemia; cutaneous T cell lymphoma excluding mycosis fungoides; anaplastic large cell lymphoma, T cell type; enteropathy-type T cell lymphoma; Adult T-cell leukemia/lymphoma; angioimmunoblastic T cell lymphoma; subcutaneous panniculitic T cell lymphoma; and peripheral T cell lymphomas that initially involve a lymph node paracortex and never grow into a true follicular pattern.

93. The method of claim 92, wherein the 10-propargyl-10-deazaaminopterin is administered in an amount of from 30 to 275 mg/m² per dose.

94. The method of claim 92, wherein the 10-propargyl-10-deazaaminopterin is administered weekly.

95. The method of claim 94, wherein the 10-propargyl-10-deazaaminopterin is administered in an amount of 30 mg/m² per dose.

96. The method of claim 94, wherein the 10-propargyl-10-deazaaminopterin is administered in an amount of from 30 to 150 mg/m² per dose.

97. The method of claim 92, wherein the 10-propargyl-10-deazaaminopterin is administered biweekly.

98. The method of claim 97, wherein the 10-propargyl-10-deazaaminopterin is administered in an amount of from 135 to 275 mg/m² per dose.

99. The method of claim 92, wherein the 10-propargyl-10-deazaaminopterin is administered in one or more seven-week cycles, each cycle comprising administration once weekly for six weeks in an amount of from 30 to 150 mg/m² per dose followed by a one week rest.

100. The method of claim 99, wherein the 10-propargyl-10-deazaaminopterin is administered in an amount of 30 mg/m² per dose.

101. The method of claim 100, further comprising supplementation with folic acid and vitamin $B_{12}$.

102. The method of claim 69, wherein the human treated has relapsed or refractory peripheral T cell lymphoma.

103. The method of claim 102, wherein the composition is administered as an injectable solution.

104. The method of claim 102, wherein the 10-propargyl-10-deazaaminopterin is administered in an amount of from 30 to 275 mg/m² per dose.

105. The method of claim 102, wherein the 10-propargyl-10-deazaaminopterin is administered weekly.

106. The method of claim 95, wherein the 10-propargyl-10-deazaaminopterin is administered in an amount of 30 mg/m² per dose.

107. The method of claim 95, wherein the 10-propargyl-10-deazaaminopterin is administered in an amount of from 30 to 150 mg/m² per dose.

108. The method of claim 102, wherein the 10-propargyl-10-deazaaminopterin is administered biweekly.

109. The method of claim 108, wherein the 10-propargyl-10-deazaaminopterin is administered in an amount of from 135 to 275 mg/m² per dose.

110. The method of claim 102, wherein the 10-propargyl-10-deazaaminopterin is administered in one or more cycles, each cycle comprising administration once weekly for six weeks in an amount of from 30 to 150 mg/m² per dose followed by a one week rest.

111. The method of claim 110, wherein the 10-propargyl-10-deazaaminopterin is administered in an amount of 30 mg/m² per dose.

112. The method of claim 69, wherein the peripheral T cell lymphoma is Sézary syndrome.

113. A method for treatment of peripheral T cell lymphoma excluding mycosis fungoides comprising administering to a human having a peripheral T cell lymphoma other than mycosis fungoides a composition comprising a therapeutically effective amount of 10-propargyl-10-deazaaminopterin, wherein the composition is formulated with 10-propargyl-10-deazaaminopterin in salt form substantially free of 10-deazaaminopterin.

114. The method of claim 113, wherein the 10-propargyl-10-deazaaminopterin is administered in an amount of from 30 to 275 mg/m² per dose.

115. The method of claim 113, wherein the 10-propargyl-10-deazaaminopterin is administered weekly.

116. The method of claim 115, wherein the 10-propargyl-10-deazaaminopterin is administered in an amount of 30 mg/m² per dose.

117. The method of claim 115, wherein the 10-propargyl-10-deazaaminopterin is administered in an amount of from 30 to 150 mg/m² per dose.

118. The method of claim 113, wherein the 10-propargyl-10-deazaaminopterin is administered biweekly.

119. The method of claim 118, wherein the 10-propargyl-10-deazaaminopterin is administered in an amount of from 135 to 275 mg/m² per dose.

120. The method of claim 113, wherein the composition is administered as an oral liquid or as an injectable solution.

121. The method of claim 113, wherein the peripheral T cell lymphoma is a Human T-lymphotropic virus (HTLV) Associated T-cell Lymphoma/leukemia.

122. The method of claim 121, wherein the composition is administered as an oral liquid or injectable solution.

123. The method of claim 121, wherein the 10-propargyl-10-deazaaminopterin is administered in an amount of from 30 to 275 mg/m² per dose.

124. The method of claim 121, wherein the 10-propargyl-10-deazaaminopterin is administered weekly.

125. The method of claim 124, wherein the 10-propargyl-10-deazaaminopterin is administered in an amount of 30 mg/m² per dose.

126. The method of claim 124, wherein the 10-propargyl-10-deazaaminopterin is administered in an amount of from 30 to 150 mg/m² per dose.

127. The method of claim 121, wherein the 10-propargyl-10-deazaaminopterin is administered biweekly.

128. The method of claim 126, wherein the 10-propargyl-10-deazaaminopterin is administered in an amount of from 135 to 275 mg/m² per dose.

129. The method of claim 113, wherein the peripheral T cell lymphoma is a subcutaneous Panniculitic T-cell Lymphoma.

130. The method of claim 129, wherein the composition is administered an oral liquid or as an injectable solution.

131. The method of claim 129, wherein the 10-propargyl-10-deazaaminopterin is administered in an amount of from 30 to 275 mg/m² per dose.

132. The method of claim 131, wherein the 10-propargyl-10-deazaaminopterin is administered weekly.

133. The method of claim 132, wherein the 10-propargyl-10-deazaaminopterin is administered in an amount of 30 mg/m² per dose.

134. The method of claim 132, wherein the 10-propargyl-10-deazaaminopterin is administered in an amount of from 30 to 150 mg/m² per dose.

135. The method of claim 131, wherein the 10-propargyl-10-deazaaminopterin is administered biweekly.

136. The method of claim 135, wherein the 10-propargyl-10-deazaaminopterin is administered in an amount from 135 to 275 mg/m² per dose.

137. The method of claim 113, wherein the peripheral T cell lymphoma is selected from: T cell prolymphocytic leukemia; T-cell granular lymphocytic leukemia; aggressive NK-cell leukemia; cutaneous T cell lymphoma excluding mycosis fungoides; anaplastic large cell lymphoma, T cell type; enteropathy-type T cell lymphoma; Adult T-cell leukemia/lymphoma; angioimmunoblastic T cell lymphoma; subcutaneous panniculitic T cell lymphoma; and peripheral T cell lymphomas that initially involve a lymph node paracortex and never grow into a true follicular pattern.

138. The method of claim 137, wherein the 10-propargyl-10-deazaaminopterin is administered in an amount of from 30 to 275 mg/m² per dose.

139. The method of claim 137, wherein the 10-propargyl-10-deazaaminopterin is administered weekly.

140. The method of claim 139, wherein the 10-propargyl-10-deazaaminopterin is administered in an amount of 30 mg/m² per dose.

141. The method of claim 139, wherein the 10-propargyl-10-deazaaminopterin is administered in an amount of from 30 to 150 mg/m² per dose.

142. The method of claim 137, wherein the 10-propargyl-10-deazaaminopterin is administered biweekly.

143. The method of claim 142, wherein the 10-propargyl-10-deazaaminopterin is administered in an amount of from 135 to 275 mg/m² per dose.

144. The method of claim 137, wherein the 10-propargyl-10-deazaaminopterin is administered in one or more seven-week cycles, each cycle comprising administration once weekly for six weeks in an amount of from 30 to 150 mg/m² per dose followed by a one week rest.

145. The method of claim 144, wherein the 10-propargyl-10-deazaaminopterin is administered in an amount of 30 mg/m² per dose.

146. The method of claim 137, further comprising supplementation with folic acid and vitamin $B_{12}$.

147. The method of claim 113, wherein the human treated has relapsed or refractory peripheral T cell lymphoma.

148. The method of claim 147, wherein the composition is administered as an injectable solution.

149. The method of claim 147, wherein the 10-propargyl-10-deazaaminopterin is administered in an amount of from 30 to 275 mg/m² per dose.

150. The method of claim 147, wherein the 10-propargyl-10-deazaaminopterin is administered weekly.

151. The method of claim 150, wherein the 10-propargyl-10-deazaaminopterin is administered in an amount of 30 mg/m² per dose.

152. The method of claim 150, wherein the 10-propargyl-10-deazaaminopterin is administered in an amount of from 30 to 150 mg/m² per dose.

153. The method of claim 147, wherein the 10-propargyl-10-deazaaminopterin is administered biweekly.

154. The method of claim 153, wherein the 10-propargyl-10-deazaaminopterin is administered in an amount of from 135 to 275 mg/m² per dose.

155. The method of claim 147, wherein the 10-propargyl-10-deazaaminopterin is administered in one or more cycles, each cycle comprising administration once weekly for six weeks in an amount of from 30 to 150 mg/m² per dose followed by a one week rest.

156. The method of claim 155, wherein the 10-propargyl-10-deazaaminopterin is administered in an amount of 30 mg/m² per dose.

157. The method of claim 113, wherein the peripheral T cell lymphoma is Sézary syndrome.

158. The method of claim 113, wherein the peripheral T cell lymphoma is Adult T cell leukemia/lymphoma associated with Human T-lymphotropic virus-1 (HTLV-1).

159. The method of claim 113, wherein the 10-propargyl-10-deazaaminopterin is administered in one or more seven-week cycles, each cycle comprising administration once weekly for six weeks in an amount of from 30 to 150 mg/m² per dose followed by a one week rest.

160. The method of claim 159, wherein the 10-propargyl-10-deazaaminopterin is administered in an amount of 30 mg/m² per dose.

161. The method of claim 113, further comprising supplementation with folic acid and vitamin $B_{12}$.

* * * * *

UNITED STATES PATENT AND TRADEMARK OFFICE
CERTIFICATE OF CORRECTION

PATENT NO. : 7,622,470 B2  Page 1 of 1
APPLICATION NO. : 11/141868
DATED : November 24, 2009
INVENTOR(S) : O'Connor et al.

It is certified that error appears in the above-identified patent and that said Letters Patent is hereby corrected as shown below:

Column 8, Claim 15, Line 2 should read - ... lymphoma is a Human T-lymphotropic virus (HTLV) ...

Column 10, Claim 69, Line 31-32 should read - ... effective amount of a salt form of 10-propargyl-10-deazaaminopterin.

Column 11, Claim 88, Line 13 should read - The method of claim 87, wherein the 10-propargyl-10- ...

Column 11, Claim 89, Line 16 should read - The method of claim 87, wherein the 10-propargyl-10- ...

Column 12, Claim 106, Line 3 should read - The method of claim 105, wherein the 10-propargyl- ...

Column 12, Claim 107, Line 6 should read - The method of claim 105, wherein the 10-propargyl- ...

Column 13, Claim 128, Line 1 should read - The method of claim 127, wherein the 10-propargyl- ...

Signed and Sealed this

Sixteenth Day of March, 2010

David J. Kappos
*Director of the United States Patent and Trademark Office*